United States Patent [19]
Engelhardt et al.

[11] Patent Number: 4,847,294
[45] Date of Patent: Jul. 11, 1989

[54] DERIVATIVES OF 2-(SUBSTITUTED SULFAMYL)-6-NITROBENZOIC ACIDS, USEFUL AS ADJUNCTS TO RADIATION THERAPY

[75] Inventors: Edward L. Engelhardt, Gwynedd Valley; Walfred S. Saari, Lansdale, both of Pa.

[73] Assignee: Merck & Co., Inc., Rahway, N.J.

[21] Appl. No.: 56,631

[22] Filed: Jun. 1, 1987

Related U.S. Application Data

[60] Division of Ser. No. 921,718, Oct. 21, 1986, Pat. No. 4,694,020, Continuation-in-part of Ser. No. 795,569, Nov. 6, 1985, Pat. No. 4,647,588, Continuation-in-part of Ser. No. 795,564, Nov. 6, 1985, Pat. No. 4,654,369, Continuation-in-part of Ser. No. 716,886, Mar. 27, 1985, abandoned.

[51] Int. Cl.[4] .............................................. A61K 31/24
[52] U.S. Cl. .................................................... 514/535
[58] Field of Search ............... 514/183, 424, 210, 357, 514/535

[56] References Cited

U.S. PATENT DOCUMENTS

| | | | |
|---|---|---|---|
| 4,603,133 | 7/1986 | Englehardt et al. | 514/229 |
| 4,647,588 | 3/1987 | Englehardt et al. | 514/535 |
| 4,654,369 | 5/1987 | Saari | 514/535 |
| 4,694,020 | 9/1988 | Englehardt et al. | 514/535 |
| 4,731,369 | 3/1988 | Englehardt et al. | 514/424 |

OTHER PUBLICATIONS

Haliwell, B. et al. Free Redicals in Biology and Medicine, Oxford 1985, pp. 238–241.
Narayanan, V. L. et al., Development of Radiosensitizers, 19 pp. 174–175 (1982).
Wardman, P. Radiation Chemistry in the Clinic: Hypoxic Cell Radiosenisitizers for Radiotherapy.

*Primary Examiner*—Richard A. Schwartz
*Assistant Examiner*—E. Brendan Magrab
*Attorney, Agent, or Firm*—Charles M. Caruso; Roy D. Meredith; Hesna J. Pfeiffer

[57] ABSTRACT

Derivatives of 2-(Substituted sulfamyl) 6-nitrobenzoic acids are disclosed, wherein at least one of the sulfamyl substituents is selected from amino-(lower alkyl), (lower alkyl)-amino-(lower alkyl), or di(lower alkyl)-amino-(lower alkyl), hydrogen, lower alkyl, hydroxy-(lower alkyl), allyl, or when taken together with the nitrogen of the sulfamyl moiety, form a heterocyclic ring. These compounds have activity in increasing the sensitivity of hypoxic tumor cells to therapeutic radiation. Also disclosed are methods of preparing such compounds and pharmaceutical compositions including such compounds.

6 Claims, No Drawings

DERIVATIVES OF 2-(SUBSTITUTED SULFAMYL)-6-NITROBENZOIC ACIDS, USEFUL AS ADJUNCTS TO RADIATION THERAPY

CROSS REFERENCE TO OTHER APPLICATIONS

This is a division of application Ser. No. 921,718, filed Oct. 21, 1986 now issued U.S. Pat. No. 4,684,090; which in turn is a continuation-in-part of application Ser. No. 795,569, filed Nov. 6, 1985, now issued U.S. Pat. No. 4,647,588; which in turn is a continuation-in-part 795,564, filed Nov. 6, 1985, now issued U.S. Pat. No. 4,559,369; which in turn is a continuation-in part of Ser. No. 716,886 now abandoned.

BACKGROUND OF THE INVENTION

This invention relates to derivatives of 2-(substituted sulfamyl)-6-nitrobenzoic acids, specifically esters, amides and hypoxic tumor cells to therapeutic radiation. It also relates to the process of preparing such compounds starting with a 2-chlorosulfonyl-6-nitro benzoate ester and aminating said 2-chlorosulfonyl benzoate ester to produce the corresponding 2-(substituted sulfamyl)-6-nitrobenzoic ester, and converting said ester to the substituted carboxamide.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, and are believed to have a more favorable therapeutic ratio.

DETAILED DESCRIPTION OF THE INVENTION

The compositions of the present invention are nitrobenzenesulfonamide compounds of the formula

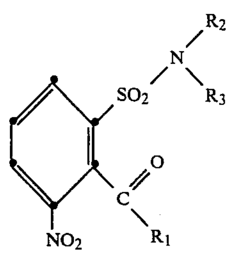

I wherein $R_1$ is hydroxy, hydroxy-(lower alkoxy), lower alkoxy, alkoxy-(lower alkoxy), allyloxy, amino, monoalkylamino, dialkylamino, hydroxyalkylamino, di(hydroxyalkyl)-amino, or allylamino.

$R_2$ and $R_3$ are each separately hydrogen, lower alkyl from 1-4 carbon atoms, hydroxy-(lower alkyl), allyl, amino-(lower alkyl), (lower alkyl)-amino-(lower alkyl), di(lower alkyl)amino-(lower alkyl), (hydroxyalkyl)-amino(loweralkyl), (hydroxyalkyl)-alkylamino(loweralkyl) or di(hydroxyalkyl)-amino(loweralkyl) or when taken together along with the nitrogen to which they are attached represent a heterocyclic ring selected from morpholino, aziridinyl, azetidinyl, pyrrolidyl, piperidyl, or $R_4$-substituted-3-oxopiperazin-1-yl

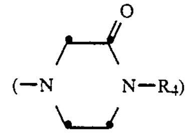

wherein $R_4$ is hydrogen, lower alkyl of from 1-4 carbons, or hydroxyalkyl of from 2-4 carbons.

The 2-(substituted sulfamyl) derivatives of 6-nitrobenzoic acid, ester and amide compounds of the present invention are prepared in the following manner:

A substituted nitrobenzoate ester or nitrobenzamide having a 2-chlorosulfonyl substituent in an aprotic solvent such as tetrahydrofuran, dioxane, dimethoxyethane, or chloroform is treated with at least an equimolar amount of an amine of the formula

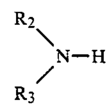

II wherein $R_2$ and $R_3$ are as described hereinabove.

It is preferred to carry out the reaction in the presence of a base in sufficient amount to neutralize the hydrogen chloride formed in the course of the reaction. The base utilized may be a tertiary amine such as triethylamine or pyridine. On the other hand the same results may be produced by adding at least twice the molar amount of reactant amine theorectically required. In this event, the reactant amine is utilized both to form the sulfonamide and to neutralize the hydrogen chloride formed in the amination reaction.

The temperature at which the reaction is carried out is not critical and may vary from 0°-100° C. or at the reflux temperature of the solvent, if under 100° C. The reaction temperature is preferably maintained at about 0-25° C. for a period of 1-24 hours. The amination reaction may be formulated as follows:

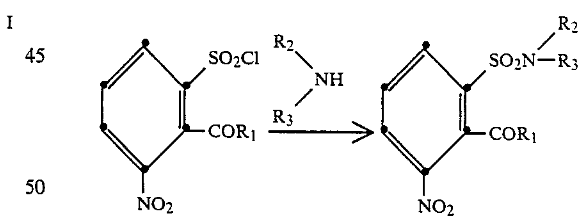

wherein $R_1$, $R_2$ and $R_3$ are as defined hereinabove.

The starting materials for the process are either known or are readily prepared from the known 2-amino-6-nitrobenzoic acid by a process of esterification followed by diazotization of the amino group and treating the formed diazonium compound with $SO_2$ in the presence of $CuCl_2$ whereby the desired starting 2-chlorosulfonyl-6-nitrobenzoate ester is formed.

The ester derivatives of this invention may also be prepared by esterification of a carboxylic acid of formula I ($R_1$=OH). Established methods for the esterification of carboxylic acids containing basic groups may be used. These include reaction with diazoalkanes or with alcohols under strongly acidic conditions.

The benzamide derivatives of this invention may be prepared by reaction of a 2-monosubstituted sulfamyl-6- nitrobenzoate ester of formula III or a 2-substituted-4-nitro-2H-1,2-benzisothiazol-3-one 1,1-dioxide of formula IV with at least one equivalent of ammonia or a mono- or dialkyl-substituted amine of formula II.

III

IV

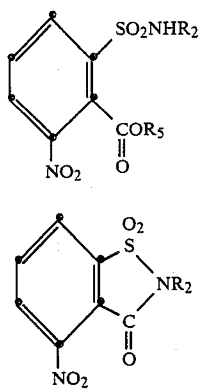

In formulas III and IV, $R_2$ is as described hereinabove and $R_5$ is either lower alkyl or hydroxy-(lower alkyl). The reaction is carried out in a suitable solvent such as a lower aliphatic alcohol or a polar aprotic solvent such as dimethylformamide, dimethylsulfoxide or others such as tetrahydrofuran, glyme, diglyme, chloroform or methylenechloride. The reaction temperature is not critical and may vary from 0°-100° C., preferably from about 25°-50° C. for a period of 1 to 10 days. When low boiling amines are used, the reaction may be run in a sealed vessel.

The compounds of this invention may also be prepared by alkylation of an amine with an amide or ester of formula V wherein $R_1$ and $R_2$ are as defined hereinabove and $R_6$ is an alkylating moiety such as haloalkyl, alkylsulfonyloxyalkyl or arylsulfonyloxyalkyl.

V

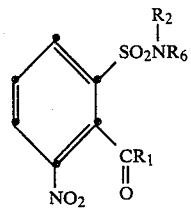

The reaction is carried out in a suitable aprotic solvent such as dimethylformamide, acetonitrile or the like. The reaction temperature may vary from 50° C. to the boiling point of the solvent for a period of 1 to 10 days. When low boiling amines are used, the reaction may be run in a sealed vessel. It is preferred to carry out the reaction in the presence of a base in sufficient amount to neutralize the acid formed in the course of the reaction. The base utilized may be a tertiary amine such as a trialkylamine or pyridine. Alternatively, at least twice the molar amount of reactant amine theoretically required may be used. In this event, the reactant amine is utilized both to form the desired product and to neutralize the acid formed in the amination reaction.

The alkylating agents of formula V are readily prepared from the corresponding alcohols by established methods.

The method of treatment of human patients or domestic animals undergoing radiation treatment of malignant disease processes employs the compounds of the present invention in pharmaceutical compositions that are administered orally or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLES

Part A—Examples of compounds in which at least one of $R_2$ and $R_3$ is a basic substituent.

EXAMPLE 1

Step A: Methyl 2-Amino-6-nitrobenzoate

A mixture of 2-amino-6-nitrobenzoic acid (11.9 g, 65.3 mmol), methyl p-toluenesulfonate (15.1 g, 81.1 mmol) and triethylamine (6.60 g, 65.3 mmol) in DMF (170 ml) was stirred under $N_2$ at 60° for 18 hours. After removing DMF at 60° and 0.2 mm pressure, the residue was dissolved in ETOAc and washed with a saturated solution of $NaHCO_3$ followed by a saturated aqueous solution of NaCl. The EtOAc extract was dried ($Na_2SO_4$), filtered and concentrated under reduced pressure. Flash chromatography over silica gel and elution with 50% toluene-50% $CHCl_3$ gave methyl 2-amino-6-nitrobenzoate (7.6 g, 59.4%), m.p. 105–107°.

Step B: Methyl 2-Chlorosulfonyl-6-nitrobenzoate

To a suspension of methyl 2-amino-6-nitrobenzoate (7.6 g, 38.7 mmol) in glacial acetic acid (37 ml) and conc. HCl (67 ml), cooled to −5°, was added slowly a solution of sodium nitrite (2.86 g, 41,4 mmol) in $H_2O$ (11.2 ml). After addition was complete, the mixture was stirred at −5° to 0° for an additional 30 minutes. During this time, a solution of $CuCl_2.2H_2O$ (2.45 g) in $H_2O$ (8.5 ml) was prepared and added to a cold solution of $SO_2$ (25 g, 0.39 mol) in glacial acetic acid (50 ml). The diazonium salt solution was then added in portions to the cooled $SO_2$—$CuCl_2$ mixture. After stirring in an ice bath for 3 hours, the reaction mixture was allowed to warm to 20°-25° and was stirred at this temperature for 18 hours. The reaction mixture was then poured onto ice (500 g), the precipitated tan solid removed by filtration and dried to give the sulfonyl chloride (9.1 g, 84.3%), m.p. 152-4°.

EXAMPLE 2

Methyl 2-[N-(2-Dimethylaminoethyl)aminosulfonyl]-6-nitrobenzoate Hydrochloride and 2-[N-(2-Dimethylaminoethyl)aminosulfonyl]-6-nitrobenzoic acid A solution of methyl 2-chlorosulfonyl-6-nitrobenzoate (500 mg, 1.79 mmol) and 2-dimethylaminoethylamine (316 mg, 3.58 mmol) in THF (35 ml) was stirred in an ice bath for 1 hour then at 20-25° for 18 hours. After removing THF under reduced pressure, the residue was partitioned between saturated $Na_2CO_3$ solution and EtOAc. The organic extract was washed (saturated NaCl solution), dried ($Na_2SO_4$), filtered and concentrated under reduced pressure. Chromatography over silica gel (elution with 5% MeOH-95% $CHCl_3$) gave an oil which when triturated with EtOAc afforded 2-[N-(2-dimethylaminoethyl)aminosulfonyl]-6-nitrobenzoic acid (90 mg, 16%), m.p. 193° decomposed with effervescence.

Treatment of the EtOAc soluble fraction with anhydrous EtOH-HC1 and recrystallization from EtOH-EtOAc gave the HCl salt of the methylester (250 mg, 38%), m.p. 170-173°.

EXAMPLE 3

N,N-Dimethyl-2-[N-(2-dimethylaminoethyl)aminosulfonyl]-6-nitrobenzamide Hydrochloride A solution of methyl 2-[N-(2-dimethylaminoethyl-)aminosulfonyl]-6-nitrobenzoate (200 mg, 0.544 mmol) and 0.5 ml of a 40% aqueous dimethylamine solution in methanol (5 ml) was allowed to stand at 20-25° for 18 hours. After concentrating under reduced pressure, the residue was treated with anhydrous ethanolic hydrogen chloride and recrystallized from MeOH-EtOAc to give the HCl salt m.p. 166-69°.

EXAMPLE 4

N,N-Dimethyl-2-[N-(2-dimethylaminoethyl)-N-(2-hydroxyethyl)aminosulfonyl]-6-nitrobenzamide Hydrochloride

Step A:

N,N-Dimethyl-2-[N-(2-dimethylaminoethyl)-N-(2-(2-tetrahydro-2H-pyranyloxy)ethyl)aminosulfonyl]-6-nitrobenzamide To a suspension of N,N-dimethyl-2-[N-(2-dimethylaminoethyl)aminosulfonyl]-6-nitrobenzamide hydrochloride (347 mg, 0.91 mmol) in DMF (5 ml) under $N_2$ was added 50% NaH (87 mg, 1.82 mmol). After stirring at 20-25° for 15 minutes until all of the NaH had reacted, a solution of 2-(2-bromoethoxy)tetrahydro-2H-pyran in DMF (2 ml) was added. The solution was stirred at 20-25° under $N_2$ for 20 hours and then concentrated under reduced pressure to remove most of the DMF. The residue was partitioned between EtOAc and a saturated aqueous solution of NaCl. After drying ($Na_2SO_4$) the EtOAc extract, filtering and concentrating, the residue was chromatographed over silica gel.

Elution with 7% MeOH-93% $CHCl_3$ gave 100 mg of product.

Step B:

N,N-Dimethyl-2-[N-(2-dimethylaminoethyl)-N-(2-hydroxyethyl)aminosulfonyl]-6-nitrobenzamide Hydrochloride A solution of the tetrahydropyranyl ether (100 mg) in THF (10 ml), $H_2O$ (5 ml) and HOAc (20 ml) was stirred at 50° for 24 hours. After concentrating under reduced pressure, the residue was partitioned between EtOAc and saturated $NaHC_3$ solution. The EtOAc extract was washed (saturated NaCl solution), dried ($Na_2SO_4$), filtered and cocentrated. The crude product was purified by conversion to the HCl salt and recrystallized (MeOH-EtOAc-hexane) to give 32 mg of product, m.p. 162-64° dec.

EXAMPLE 5

N,N-Dimethyl-2-{N-[2-(N-(2-hydroxyethyl)-N-methylamino)-ethyl]-N-methylaminosulfonyl}-6-nitrobenzamide Hydrogen Oxalate

Step A:

N,N-Dimethyl-2-[N-(2-methylsulfonyloxyethyl)-N-methylaminosulfonyl]-6-nitrobenzamide A solution of N,N-dimethyl-2-[N-(2-hydroxyethyl)-N-methylaminosulfonyl]-6-nitrobenzamide, prepared as described in Example 9 U.S. Ser. No. 795,569, filed Nov. 6, 1985 of Walfred Saari, incorporated herein by reference, (1.0 g, 3.0 mmol) and methanesulfonyl chloride (0.71 g, 6.2 mmol) in pyridine (10 ml) was stirred at 20-25° for one day. After concentration under reduced pressure, the residue was partitioned between ethyl acetate and 1N aqueous HCl. The ethyl acetate extracted was washed with water, dried and concentrated. Pure mesylate (1.0 g) was obtained by flash chromatography over silica gel and elution with a 1% methanol-99% chloroform solvent mixture.

Step B:

N,N-Dimethyl-2-{N-[2-(N-(2-hydroxyethyl)-N-methylamino)ethyl]-N-methylaminosulfonyl}-6-nitrobenzamide Hydrogen Oxalate A solution of N,N-dimethyl-2-[N-(2-methylsulfonyloxyethyl)-N-methylaminosulfonyl]-6-nitrobenzamide (0.50 g, 1.2 mmol) and 2-(methylamino)ethanol (0.22 g, 2.9 mmol) in acetonitrile (20 ml) was stirred at reflux for 20 hours. After concentrating under reduced pressure, the residue was partitioned between ethyl acetate and water. The ethyl acetate layer was dried ($Na_2SO_4$), filtered and concentrated. Flash chromatography of the residue over silica gel and elution with 5% methanol-95% chloroform gave 400 mg of pure product as an oil. The hydrogen oxalate salt, mp 159.0-162.0°, was prepared for analysis.

EXAMPLE 6

N,N-Dimethyl-2-[N-(2-piperidinoethyl)-N-methylaminosulfonyl]-6-nitrobenzamide Hydrochloride A solution of N,N-dimethyl-2-[N-(2-methylsulfonyloxyethyl-N-methylaminosulfonyl]-6-nitrobenzamide (0.41 g, 1.0 mmol) and piperidine (0.17 g, 2 mmol) in acetonitrile (20 ml) is stirred at reflux for 20 hours. The product is isolated following the procedure of Example 5, Step B and converted to the hydrochloride salt with anhydrous ethanolic hydrogen chloride.

EXAMPLES

Part B - Examples in which each of $R_2$ and $R_3$ is a non-basis substituent.

EXAMPLE I

Methyl 2-[N-(2-Hydroxyethyl)-N-methylaminosulfonyl]-6-nitrobenzoate

N-Methylethanolamine (2.96 g, 39.4 mmol) was added to a solution of methyl 2-chlorosulfonyl-6-nitrobenzoate (5.5 g, 19.7 mmol, prepared according to Example 1 of Part a, supra) in THF (150 ml) and the mixture stirred at 20–25° for 18 hours. After removing THF under reduced pressure, the residue was partitioned between EtOAc and $H_2O$. The organic extract was washed with saturated NaCl solution and dried ($Na_2SO_4$). Flash chromatography of the residue over silica gel and eluation with 1% MeOH-99% $CHCl_3$ afforded pure sulfonamide. Recrystallization from EtOAc-hexane gave analytically pure product (5.2 g, 82.9%), m.p. 98–101°.

EXAMPLE 2

Methyl 2-[N,N-Di(2-hydroxyethyl)aminosulfonyl]-6-nitrobenzoate

A solution of di(2-hydroxyethyl)amine (0.76 g, 7.2 mmol) in THF (10 ml) was added to a solution of methyl 2-chlorosulfonyl-6-nitrobenzoate (1.0 g. 3.6 mmol) in THF (10 ml) and the mixture stirred at 20–25° for 18 hours. After removing THF under reduced pressure, the crude product was extracted into EtOAc which was then washed ($H_2O$), dried ($Na_2SO_4$), filtered and concentrated under reduced pressure. Flash chromatography of the residue over silica gel and eluation with 5% MeOH-95% $CHCl_3$ gave pure sulfonamide. Analytically pure material (0.56 g, 44.8%), m.p. 92–3°, was obtained upon recrystallization from EtOAc-hexane.

EXAMPLE 3

Methyl 6-Nitro-2-[3-oxo-1-piperazinylsulfonyl]benzoate

Piperazin-2-one (0.36 g, 3.6 mmol) was added to a mixture of methyl 2-chlorosulfonyl-6-nitrobenzoate (1.0 g, 3. C mmol) and triethylamine (0.37 g, 3.6 mmol) in $CHCl_3$ (120 ml) and the resulting solution stirred at 20–25° for 18 hours. Removal of $CHCl_3$ under reduced pressure and flash chromatography of the residue over silica gel (elution with 5% MeOH-95% $CHCl_3$) afforded pure sulfonamide (1.2 g, 96.8%). Recrystallization from MeOH-$H_2O$ gave an analytical sample, m.p. 189–91°.

EXAMPLE 4

Methyl 2-[N-Morpholinosulfonyl]-6-nitrobenzoate

A solution of morpholine (1.25 g, 14.3 mmol) in THF (20 ml) was added over 30 minutes to a stirred, cooled solution of methyl 2-chlorosulfonyl-6-nitrobenzoate (2.0 g, 7.15 mmol) in THF (20 ml). After stirring at 20–25° for 18 hours, THF was removed under reduced pressure. The residue was partitioned between EtOAc and saturated NaCl-$H_20$ and the EtOAc extracted was washed with $H_2O$, dried ($Na_2SO_4$), filtered and concentrated. Recrystallization from MeOH-EtOH gave pure sulfonamide (1.7 g, 72%), m.p. 145–8°.

EXAMPLE 5

Methyl 2-[N-(2-Hydroxyethyl)aminosulfonyl]-6-nitrobenzoate

A solution of methyl 2-chlorosulfonyl-6-nitrobenzoate (0.50 g, 1.79 mmol) and ethanolamine (0.33 g, 5.4 mmol) in THF (20 ml) was stirred at 20–25° for 18 hours and then concentrated under reduced pressure. Product was extracted into EtOAc which was then washed ($H_2O$), dried ($Na_2SO_4$), filtered and concentrated under reduced pressure. The residue was recrystallized from EtOAc-hexane to give pure sulfonamide (0.28 g, 51.4%), m.p. 110–12°.

EXAMPLE 6

N-(2-Hydroxyethyl)-2-[N-(2-hydroxyethyl)aminosulfonyl]-6-nitrobenzamide

Step A: 2-(2-Hydroxyethyl)-4-nitro-2H-1,2-benzisothiazol-3-one 1,1-dioxide

To approximately 2 ml of ethylene oxide cooled in an ice bath was added a suspension of 4-nitro-2H-1,2-benzisothiazol-3-one 1,1-dioxide (2.0 g, 8.76 mmol) in $H_2O$ (140 ml). After stirring in the ice bath for 1 hour, the mixture was allowed to stir at 20–25° for 18 hours. Water was removed under reduced pressure and the residue flash chromatographed over silica gel. Elution with 2% isopropanol—98% $CH_2Cl_2$ gave product which was recrystallized from EtOAc-hexane to give the 2-hydroxethyl derivative (0.39 g, 16%), m.p. 140–1°.

Step B: N-(2-Hydroxyethyl)-2-[N-(2-hydroxyethyl)aminosulfonyl]-6-nitrobenzamide A solution of 2-(2-hydroxyethyl)-4-nitro-2H-1,2-benzisothiazol-3-one 1,1-dioxide (100 mg, 0.37 mmol) and ethanolamine (24 mg, 0.39 mmol) in THF (5 ml) was allowed to stand at 20–25° for 3 days. After removal of THF under reduced pressure, the residue was recrystallized from MeOH-EtOAc-hexane to give 112 mg (91%) of product, m.p. 176.5–177.5°.

EXAMPLE 7

Allyl 2-[N-Morpholinosulfonyl]-6-nitrobenzoate

Step A: Allyl 2-Amino-6-nitrobenzoate

A mixture of 2-amino-6-nitrobenzoic acid (2.0 g, 11 mmol), allyl chloride (1.05 g, 13.7 mmol) and triethylamine (1.11 g, 11 mmol) in DMF (50 ml) was stirred at 60° for 18 hours. After concentrating under reduced pressure, the residue was extracted with EtOAc which was then washed with saturated $NaHCO_3$ solution and saturated NaCl solution, dried ($Na_2SO_4$) and filtered. EtOAc was removed under reduced pressure and the residue chromatographed over silica gel. Elution with 50% hexane-50% $CHCl_3$ gave the allyl ester (1.1 g, 45%). An analytical sample, m.p. 54–5°, was obtained upon recrystallization from toluene-hexane.

Step B: Allyl 2-Chlorosulfonyl-6-nitrobenzoate

To a suspension of allyl 2-amino-6-nitrobenzoate (3.3 g, 14.9 mmol) in glacial acetic acid (80 ml) and conc. HCl (26 ml) cooled to −5 was added slowly a solution of sodium nitrite (1.10 g, 15.9 mmol) in $H_2O$ (6 ml).

After addition was complete, the mixture was stirred at −5 to 0° for an additional 30 minutes. This diazonium salt solution was then added in portions to a cold solution of $SO_2$ (10 g, 0.156 mol) and $CuCl_2.2H_2O$ (1.19 g) in acetic acid (20 ml) and $H_2O$ (4 ml). After stirring in an ice bath for 3 hours, the reaction mixture was allowed to warm to 20–25° and then poured on to ice (500 g). The solid sulfonyl chloride was filtered off and dried to give 3.5 g (77.4%) of product, m.p. 68–70°. An analytical sample, m.p. 70–72°, was obtained upon recrystallization from n-butyl chloride-hexane.

Step C: Allyl 2-[N-Morpholinosulfonyl]-6-nitrobenzoate

A solution of morpholine (1.63 g, 18.7 mmol) in THF (30 ml) was added over 25 minutes to a stirred and cooled solution of allyl 2-chlorosulfonyl-6-nitrobenzoate (2.85 g, 9.3 mmol) in THF (80 ml). After stirring at 20–25° for 18 hours, THF was removed under reduced pressure and the residue partitioned between EtOAc and saturated NaCl solution. The EtOAc extract was dried ($Na_2SO_4$) filtered and concentrated to give a quantitative yield of the sulfonamide, m.p. 145–7°. An analytical sample, m.p. 150–2° was obtained upon recrystallization from MeOH.

EXAMPLE 8

N,N-Dimethyl-2-[N-(2-hydroxyethyl)aminosulfonyl]-6-nitrobenzamide

A solution of methyl 2-[N-(2-hydroxyethyl)aminosulfonyl]-6-nitrobenzoate (4.58 g, 15.1 mmol) in absolute MeOH (50 ml) was added to a solution of dimethylamine (6.8 g, 0.15 mol) and potassium tertbutoxide (0.68 ml of a 0.262 M soluton in tertbutanol) in absolute MeOH (100 ml). After stirring at 20–25° for 4 days, solvents were removed under reduced pressure. The residue was dissolved in EtOAc and washed with 0.5N HCl followed by a saturated aqueous NaCl solution. The EtOAc extract was dried ($Na_2SO_4$), filtered and concentrated to give 4.2 g (88%) of product.

EXAMPLE 9

N,N-Dimethyl-2-[N-(2-hyroxyethyl)-N-methylaminosulfonyl]-6-nitrobenzamide

A solution of N,N-Dimethyl-2-[N-(2-hydroxyethyl-)aminosulfonyl]-6-nitrobenzamide (3.97 g, 12.5 mmol) in dry DMF (40 ml) was added slowly to a stirred suspension of 50% NaH (0.60 g, 12.5 mmol) in dry DMF (10 ml) under $N_2$ at 20–25°. After formation of the sodium salt was complete, a solution of methyl p-toluenesulfonate (2.40 g, 12.9 mmol) in DMF (4 ml) was added and the reaction mixture stirred at 20–25° for 20 hours and then at 60° for 23 hours. The orange solution was mixed with EtOAc (400 ml) and the white solid which formed was filtered off. This precipitate was washed with EtOAc (100 ml). The combined EtOAc solutions were washed with a saturated aqueous NaCl solution, dried ($Na_2SO_4$), filtered and concentrated under reduced pressure. Pure produced, mp 107–08°, 2.5 g (60%) was obtained by flash chromatography over silica gel and elution with a 65% n-butylchloride-35% acetonitrile solvent mixture.

EXAMPLE 10

Methyl 2-[N-(3-Hydroxypropyl)aminosulfonyl]-6-nitrobenzoate

A solution of methyl 2-chlorosulfonyl-6-nitrobenzoate (2.80g, 10 mmol) in 100 ml of THF was cooled to ice temperature and stirred in an ice-bath while a solution of 3-amino-1-propanol (99%) (1.67g, 22 mmol) was added dropwise over a period of 45 minutes. Stirring in the ice-bath was continued for 30 minutes. The reaction miture than was acidified by addition of 3.0 ml of 1.2N HCl. The THF was evaporated under reduced pressure and the residue taken up in 100 ml of ethyl acetate. After extracting this solution with 4×20 ml of saturated NaCl solution, the ethyl acetate was evaporated and the residue recrystallized from a mixture of ethyl acetate and hexane to give 2.70g (84.9%) of light yellow crystalline product, m.p., 87–88.5°.

EXAMPLE 11

Methyl 2-[N-(2-Hydroxy-1-propyl)aminosulfonyl]-6-nitrobenzoate

A solution of methyl 2-chlorosulfonyl-6-nitrobenzoate (2.80g, 10 mmol) in 100 ml of THF was cooled in an ice-bath and stirred while a solution of 1-amino-2-propanol (1.65g, 22 mmol) in 10 ml of THF was added dropwise over a period of 50 minutes. After stirring an additional 30 minutes in the ice-bath, the reaction mixture was acidified by the addition of 3 ml of 1.2N HCl. The THF was evaporated under reduced pressure and the residue taken up in 100 ml of ethyl acetate. After extracting with 4×20 ml of saturated NaCl solution, the ethyl acetate solution was dried over $Na_2SO_4$ and the solvent evaporated. The residue was crystallized from a mixture of ethyl acetate and hexane to give 2.02g (63.5%) of yellow crystalline product, m.p., 93.5–95°.

EXAMPLE 12

N,N-Dimethyl-2-[N-(3-hydroxypropyl)aminosulfonyl]-6-nitrobenzamide

Methyl 2-[N-(3-hydroxpropyl)amino sulfonyl]-6-nitrobenzoate (2.00g, 6.28 mmol) was dissolved in 60 ml. of methanol. Sodium methoxide (1.0 ml of a 0.1M solution in methanol) was added and the solution cooled in an ice-bath and stirred while a rapid stream of dimethylamine was passed into the vortex for 15 minutes. After stirring for 16½ hours, during which time the temperature rose to 25°, the methanol and excess dimethylamine were evpaorated under reduced pressure. Flash chromatography of the residue on E. Merck silica gel 60 (230–400 mesh) developed with n-butyl chloride:acetonitrile in the ratio of 65:35 gave light yellow crystalline product, isolated in two fractions, each melting at 85°–87°. The second fraction contained a small amount of a second component, visible on TLC. Recrystallization of each fraction from a mixture of ethyl acetate and hexane gave 0.48g of product, m.p., 86–87.5° and 0.43g of product, m.p., 85.5–87°. Each product was analytically pure.

EXAMPLE 13

N,N-Dimethyl-2-[N-(2-hydroxy-1-propyl)aminosulfonyl]-6-nitrobenzamide

Methyl 2-[N-(2-hydroxy-1-propyl)aminosulfonyl]-6-nitrobenzoate (2.00g, 628 mmol) was dissolved in 60 ml of methanol. Sodium methoxide (1.0 ml of a 0.1M solution in methanol) was added and the solution cooled and stirred in an ice-bath while a rapid stream of dimethylamine was passed into the vortex for 15 minutes. Stirring in the ice-bath then was continued for 1 hour, when the flash was removed from the bath and the reaction mixture allowed to stand at room temperature overnight. The methanol and excess dimethylamine then were evaporated under reduced pressure and the residue shaken with ethyl acetate, 80 ml; 0.2N HCl, 10 ml; and saturated NaCl, 10 ml. The ethyl acetate layer was separated, extracted with 3×15 ml of saturated NaCl and evaporated to give a clear yellow oil. After drying 23 hours in vacuo, this product weighed 2.03 g. Crystallization had started after 3 days. Recrystallization from a mixture of ethyl acetate and hexane gave 1.33g (63.9%) of product, m.p., 95.5–97°.

EXAMPLE 14

N,N-Dimethyl-2-[N-(3-hydroxpropyl)-N-methylaminosulfonyl]-6-nitrobenzamide

N,N-Dimethyl-2-[N-(3-hydroxypropyl)aminosulfonyl]-6-nitrobenzamide (1.37g, 4.13 mmol) in 12 ml of DMF, was added dropwise to a suspension of 198 mg (4.13 mmol) of 50% NaH in 3 ml of DMF in an atmosphere of $N_2$. When evolution of hydrogen was complete, a solution of methyl p-toluene sulfonate (0.794g, 4.14 mmol) in DMF, 2 ml, was added. the clear deep yellow solution was stirred at 25° for 17 hours, then at 60° for 23 hours. The solution then was mixed with 175 ml of ethylacetate and the precipitate that separated collected on a filter and washed with 50 ml of ethyl acetate. The combined filtrate and washings were extracted with 6×25 ml of saturated NaCl solution and the ethyl acetate evaporated to give 1.66 g of a clear yellow oil. Flash chromatography over E. Merck silica gel 60 (230–400 mesh) gave 0.49 g of a clear light yellow oil. This material was dissolved in 50 ml of $CHCl_3$, the solution extracted with 4×5 ml of 1N NaOH, then with 3×5 ml of saturated NaCl and dried over $MgSO_4$. After evaporation of the $CHCl_3$, the residue was dissolved in ethyl acetate and the solution filtered to remove a trace of $MgSO_4$. Evaporation of the solvent gave 0.44g of light yellow crystalline product, m.p., 91.5–92.5°.

ADDITIONAL EXAMPLES

Pact C

EXAMPLE 1

Ethyl 2-chlorosulfonyl-6-nitrobenzoate

Step A: Ethyl 2-Amino-6-nitrobenzoate

A solution of 2-amino-6-nitrobenzoic acid (29.2 g, 0.16 mol), diethylsulfate (24.7 g, 0.160 mol) and triethylamine (16.2 g, 0.160 mol) in N-dimethylformamide (250 ml) was stirred at 20–25° for 20 hours. After removing DMF at 60° and 0.2 mm pressure, the residue was flash chromotographed over silica gel and the ethyl ester (10.8 g) eluted first with toluene then with 50% toluene—50% chloroform.

Step B: Ethyl 2-chlorosulfonyl-6-nitrobenzoate

To a suspension of ethyl 2-amino-6-nitrobenzoate (10.8 g, 51.2 mmol) in glacial acetic acid (55 mL) and concentrated HCl (95 mL), cooled to −5°, was added slowly a solution of sodium nitrite (3.79 g, 54.9 mmol) in $H_2O$ (15 mL). After addition was complete, the mixture was stirred at −5° to 0° for an additional 30 minutes. During this time, a solution of $CuCl_2.2H_2O$ (4.10 g) in $H_2O$ (10 mL) was prepared and added to a cold soluton of $20_2$ (32 g) in glacial acetate acid (100 mL). The diazonium salt solution was added in portions to the cooled $SO_2$-$CuCl_2$ mixture. After stirring in an ice bath for 3 hours, the reaction mixture was allowed to warm to 20–25° and then poured onto ice (800 g). The precipitated solid was removed by filtration and dried to give 10.62 g (70.7 %) of the sulfonyl chloride, m.p. 102–105°. An analytical sample, m.p. 107–08°, was obtained upon recrystallization from EtOAc-hexane. Anal Calc'd for $C_9H_8ClNO_6S$: C, 36.81; H, 2.75; N, 4.77.

Found: C, 36.84; H, 2.80; N, 4.77.

Ethyl 2-[N-(2-Dimethylaminoethyl)aminosulfonyl]-6-nitrobenzoate hydrochloride

From: Ethyl 2-chlorosulfonyl-6-nitrobenzoate

A solution of N,N-dimethylethylenediamine (1.5 g, 17 mmol) and N,N-diisopropylethylamine (2.2 g, 17 mmol) in tetrahydrofuran (25 mL) was added over 15 minutes to a stirred solution of ethyl 2-chlorosulfonyl-6-nitrobenzoate (5.0 g, 17 mmol) in tetrahydrofuran (100 mL) cooled with an ice bath. After addition was complete, the reaction mixture was stirred at ice bath temperature for 1 hour, then at 20–25° for 20 hours. Tetrahydrofuran was removed under reduced pressure and the residue partitioned between ethyl acetate and water. The organic extract was dried ($Na_2SO_4$), filtered and concentrated under reduced pressure. The residue was treated with ethanolic-anhydrous hydrogen chloride and the hydrochloride salt recrystallized from methanol-ethylacetate-hexane to give 4.28 g (65.9%) of product, m.p. 165–166° dec. Anal. Calc'd for $C_{13}H_{19}N_3O_6S.HCl$: C, 40.89; H, 5.28; N, 11.00.

Found: C, 41.24; H, 5.52; N, 11.10.

From: Methyl 2-[N-(2-Dimethylaminoethyl)aminosulfonyl]-6-nitrobenzoate Hydrochloride A solution of the methyl ester hydrochloride (367 mg, 1 mmol) in absolute ethanol (20 mL) containing sodium ethoxide (1.26 mmol) was stirred at reflux for 15 hours under $N_2$. After adding glacial acetic acid (0.1 mL) and concentrating under reduced pressure, the residue was partitioned between ethyl acetate and a saturated aqueous solution of sodium chloride. The ethyl acetate extract was washed with more aqueous sodium chloride, dried ($Na_2SO_4$), filtered and concentrated. The residue was converted to the hydrochloride salt with ethanolic-anhydrous hydrogen chloride and recrystallized from ethanol-ethyl acetate-hexane to give 110 mg (28.9%) of product. m.p. 163–4°. Anal Calc'd for $C_{13}H_{19}N_3O_6S.HCl$: C, 40.89; H, 5.28; N, 11.00;

Found: C, 41.21; H, 5.47; N, 11.14.

EXAMPLE 2

Methyl 2-[N-(2-Dimethylaminoethyl)-N-(2-hydroxyethyl-)aminosulfonyl]-6-nitrobenzoate Hydrochloride A solution of N-(2-dimethylaminoethyl)ethanolamine (0.95 g, 7.15 mmol) in tetrahydrofuran (20 mL) was added over 10 minutes to a stirred solution of methyl 2-chlorosulfonyl-6-nitrobenzoate (1.0 g, 3.58 mmol) in tetrahydrofuran (30 mL) cooled with an ice bath. After addition was complete, the reaction mixture was stirred at 20–25° for 5 hours. Tetrahydrofuran was removed under reduced pressure and the residue partitioned between ethyl acetate and water. The organic extract was dried ($Na_2SO_4$), filtered and concentrated under reduced pressure. The concentrate was flash chromatographed over silica gel and product eluted with 5% methanol—95% chloroform. The hydrochloride salt, m.p. 152.5–4.5° dec, 0.63 g, (42.9%), was obtained upon treatment of the purified base with ethanolic anhydrous hydrogen chloride and recrystallization for methanol-ethyl acetate. Anal Calc'd for $C_{14}H_{21}N_3O_7S$: C, 40.82; H, 5.39; N, 10.20

Found: C, 41.00: H, 5.43; N, 10.34.

EXAMPLE 3

Isopropyl 2-[N-(2-Dimethylaminoethyl)aminosulfonyl]-6-nitrobenzoate Hydrochloride A solution of methyl 2-[N-(2-dimethylaminoethyl-)aminosulfonyl]-6-nitrobenzoate hydrochloride (12.0 g, 32.6 mmol) in dry isopropanol (500 mL) containing sodium isopropoxide (39 mmol) was stirred at reflux under $N_2$ for 18 hours. After adding glacial acetic acid (1 mL) and concentrating under reduced pressure, the residue was partitioned between ethyl acetate and water. The ethyl acetate extract was washed with a saturated aqueous solution of sodium chloride, dried ($Na_2SO_4$), filtered and concentrated. The residue was converted to the hydrochloride salt with ethanolic anhydrous hydrogen chloride and recrystallized from methanol - ethyl acetate to give 4.0 g (31%) of product, m.p. 187.0–190.0° dec. Anal Calc'd for $C_{14}H_{21}N_3O_6S.HCl$: C, 42.47; H, 5.60; N, 10.61

Found: C, 42.21; H, 5.95; N, 10.44.

EXAMPLE 4

Methyl 2-[N-(2-Piperidinoethyl)aminosulfonyl]-6-nitrobenzoate Hydrochloride

A solution of 1-(2-aminoethyl)piperidine (0.23 g, 1.79 mmol) and N,N-diisopropylethylamine (0.23 g, 1.79 mmol) in tetrahydrofuran (5 ml) is added over 15 minutes to a stirred solution of methyl 2-chlorosulfonyl-6-nitrobenzoate (0.50 g, 1.79 mmol) in tetrahydrofuran (25 ml) cooled with an ice bath. The product is isolated following the procedure of Example 1 and converted to the hydrochloride salt with anhydrous ethanolic hydrogen chloride.

The foregoing specification and examples describe the invention to the extent necessary to illustrate the principles and practice of the present invention. It will be understood that the scope of the present invention encompasses any modifications, deletions and variations as come within the present invention. The following claims also illustrate the nature of the invention.

What is claimed is:

1. A method for enhancing the therapeutic effect of radiation which comprises administering to a patient in need of such radiation treatment an effective amount of a compound or compounds of the formula

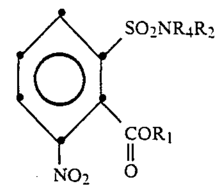

wherein $R_1$ is lower alkyl, or lower alkyl substituted with hydroxyl;

$R_2$ is lower alkyl, substituted with $$-N\begin{matrix} R_1 \\ R_3 \end{matrix}$$

is hydrogen, lower alkyl, or lower alkyl substituted with hydroxy; and $R_4$ is hydrogen or hydroxy lower alkyl;

or the hydrochloride or hydrochlorides; or physiologically acceptable salts; or mixtures thereof.

2. A method for enhancing the therapeutic effect of radiation which comprises administering to a patient in need of such radiation treatment an effective amount of a compound or compounds selected from the group consisting essentially of compounds of defined claim 1, isopropyl 2-[N-(2-dimethylaminoethyl)-aminosulfonyl]-6-nitrobenzoate, ethyl 2-[N-(2-dimethylaminoethyl-)aminosulfonyl]-6-nitrobenzoate, methyl 2-[N-dimethylaminoethyl)-N-(2-hydroxyethyl)aminosulfonyl)-6-nitrobenzoate, hydrochlorides thereof, physiologically acceptable salts thereof, and mixtures thereof.

3. A method for enhancing the therapeutic effect of radiation which comprises administering to a patient in need of such radiation treatment an effective amount of isopropyl 2-[N-(2-dimethyl aminoethyl)-aminosulfonyl]-6-nitrobenzoate, its hydrochloride, or other physiologically acceptable salts thereof.

4. A method for enhancing the therapeutic effect of radiation which comprises administering to a patient in need of such radiation treatment an effective amount of ethyl 2-[N-(2-dimethylaminoethyl)aminosulfonyl]-6-nitrobenzoate, its hydrochloride, or other physiologically acceptable salts thereof.

5. A method for enhancing the therapeutic effect of radiation which comprises administering to a patient in need of such radiation treatment an effective amount of methyl 2-[N-(2-dimethylaminoethyl)-N-(2-hydroxyethyl)aminosulfonyl)-6-nitrobenzoate, its hydrochloride, or other physiologically acceptable salts thereof.

6. A method for enhancing the therapeutic effect of radiation which comprises administering to a patient in need of such radiation treatment an effective amount of a compound or compounds of the formula

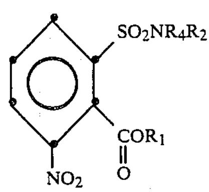

wherein $R_1$ is lower alkyl, or lower alkyl substituted with hydroxyl;

$R_2$ is lower alkyl, substituted with $$-N\begin{matrix} R_1 \\ R_3 \end{matrix};$$

$R_3$ is hydrogen, lower alkyl, or lower alkyl substituted with hydroxy; and $R_4$ is hydrogen or hydroxy lower alkyl; with the proviso that when $$-N\begin{matrix} R_1 \\ R_3 \end{matrix}$$

forms a heterocyclic ring, said ring is aziridinyl, azetidinyl, pyrrolidyl, or piperidyl; or hydrochloride or hydrochlorides; or physiologically acceptable salts; or mixtures thereof.

* * * * *